US012685456B2

(12) United States Patent　　　(10) Patent No.: US 12,685,456 B2

Chana et al.　　　(45) Date of Patent: Jul. 21, 2026

(54) NEEDLE PROBE, APPARATUS FOR SENSING COMPOSITIONAL INFORMATION, MEDICAL DRAIN, METHOD OF MEASURING A THERMAL PROPERTY, AND METHOD OF SENSING COMPOSITIONAL INFORMATION

(71) Applicant: Oxford University Innovation Limited, Oxford (GB)

(72) Inventors: Kamaljit Singh Chana, Oxfordshire (GB); Parvinderpal Singh Sains, Thames Ditton (GB)

(73) Assignee: Oxford University Innovation Limited, Oxford (GB)

( * ) Notice: Subject to any disclaimer, the term of this patent is extended or adjusted under 35 U.S.C. 154(b) by 1119 days.

(21) Appl. No.: 17/658,601

(22) Filed: Apr. 8, 2022

(65) Prior Publication Data

US 2022/0225890 A1　　Jul. 21, 2022

Related U.S. Application Data

(60) Division of application No. 16/156,943, filed on Oct. 10, 2018, now Pat. No. 11,324,416, which is a
(Continued)

(30) Foreign Application Priority Data

Apr. 15, 2016　(GB) ..................................... 1606624

(51) Int. Cl.
　　*A61B 5/0537*　　(2021.01)
　　*A61B 5/00*　　(2006.01)
　　(Continued)

(52) U.S. Cl.
　　CPC .............. *A61B 5/0537* (2013.01); *A61B 5/01* (2013.01); *A61B 5/444* (2013.01); *A61B 5/4869* (2013.01);
　　(Continued)

(58) Field of Classification Search
　　CPC ......... A61B 5/0537; A61B 5/01; A61B 5/444; A61B 5/4869; A61B 5/6848;
　　(Continued)

(56) References Cited

U.S. PATENT DOCUMENTS 2,562,129 A　7/1951　Shcherer et al.
3,698,394 A　10/1972　Piper et al.
(Continued)

FOREIGN PATENT DOCUMENTS

EP　　0208096　　1/1987
EP　　0280229　　1/1990
(Continued)

OTHER PUBLICATIONS

Niu et al. 'A New Approach for the Determination of Fish Freshness by Electrochemical Impedance Spectroscopy' Journal of Food Science— vol. 65, No. 5, 2000 (Year: 2000).*
(Continued)

*Primary Examiner* — Patrick Fernandes
(74) *Attorney, Agent, or Firm* — Levine Bagade Han LLP

(57) ABSTRACT

The invention relates to sensing compositional information about material by measuring thermal properties of the material. In one arrangement there is provided a needle probe for sensing compositional information. The probe comprises a needle having a tip region. A resistive element is attached to the needle at the tip region. A measurement system is configured to: 1) drive an electrical current through the resistive element to apply heating to the resistive element, and 2) measure an electrical response of the resistive ele-
(Continued)

ment to the heating. A processing unit analyses the measured electrical response of the resistive element to the heating to determine compositional information about material in contact with the tip region.

6 Claims, 8 Drawing Sheets

Related U.S. Application Data continuation of application No. PCT/GB2017/051024, filed on Apr. 12, 2017.

(51) Int. Cl.

| | | |
|---|---|---|
| *A61B 5/01* | (2006.01) | |
| *A61B 10/02* | (2006.01) | |
| *A61M 5/32* | (2006.01) | |
| *A61M 27/00* | (2006.01) | |
| *G01N 25/00* | (2006.01) | |
| *G01N 27/18* | (2006.01) | |
| *G01N 33/02* | (2006.01) | |

(52) U.S. Cl.
CPC ........ *A61B 5/6848* (2013.01); *A61B 10/0233* (2013.01); *A61M 5/329* (2013.01); *A61M 27/002* (2013.01); *G01N 25/00* (2013.01); *G01N 33/02* (2013.01); *A61M 2205/3653* (2013.01); *G01N 27/18* (2013.01)

(58) Field of Classification Search
CPC . A61B 10/0233; A61M 5/329; A61M 27/002; A61M 2205/3653; G01N 25/00; G01N 27/18
See application file for complete search history.

(56) References Cited

U.S. PATENT DOCUMENTS

| | | | |
|---|---|---|---|
| 4,220,041 A | 9/1980 | Potter | |
| 4,513,749 A * | 4/1985 | Kino | G01H 5/00 600/549 |
| 4,869,596 A | 9/1989 | Klein et al. | |
| 4,960,109 A * | 10/1990 | Lele | A61N 7/02 601/3 |
| 5,044,767 A | 9/1991 | Gustafsson | |
| 5,330,268 A | 7/1994 | Klein et al. | |
| 5,795,064 A | 8/1998 | Mathis | |
| 6,181,970 B1 * | 1/2001 | Kasevich | A61B 18/1815 607/101 |
| 6,308,564 B1 | 10/2001 | Wehrmeyer et al. | |
| 6,419,635 B1 * | 7/2002 | Hedengren | A61B 5/01 600/549 |
| 6,676,287 B1 | 1/2004 | Mathis et al. | |
| 7,048,436 B2 | 5/2006 | Mathis | |
| 9,017,258 B2 | 4/2015 | Ollmar et al. | |
| 9,182,364 B1 | 11/2015 | Condie et al. | |
| 9,636,035 B2 | 5/2017 | Ollmar et al. | |
| 11,324,416 B2 | 5/2022 | Chana et al. | |
| 2002/0026188 A1 | 2/2002 | Balbierz et al. | |
| 2004/0165645 A1 | 8/2004 | Mathis | |
| 2005/0105583 A1 | 5/2005 | Xiao et al. | |
| 2007/0127543 A1 | 6/2007 | Petrovic | |
| 2010/0204928 A1 | 8/2010 | Lepsch et al. | |
| 2011/0245713 A1 | 10/2011 | Rensen et al. | |
| 2012/0116242 A1 | 5/2012 | Mahajan et al. | |
| 2014/0031758 A1 | 1/2014 | Lee et al. | |
| 2014/0369379 A1 | 12/2014 | Emanuel et al. | |
| 2019/0038176 A1 | 2/2019 | Chan et al. | |
| 2025/0331730 A1 | 10/2025 | Chana et al. | |

FOREIGN PATENT DOCUMENTS

| | | |
|---|---|---|
| EP | 0406282 | 1/1991 |
| EP | 1946713 | 7/2008 |
| EP | 2391268 | 12/2011 |
| EP | 2494331 | 9/2012 |
| JP | 2001-174424 | 6/2001 |
| JP | 2015-119895 | 7/2015 |
| KR | 2005-0080968 | 8/2005 |
| WO | WO 2000/070333 | 11/2000 |
| WO | WO 2003/002998 | 1/2003 |
| WO | WO 2006/063427 | 6/2006 |
| WO | WO 2007/074422 | 7/2007 |
| WO | WO 2011/065877 | 6/2011 |
| WO | WO 2012/131281 | 10/2012 |

OTHER PUBLICATIONS

Beetner et al. 'Differentiation Among Basal Cell Carcinoma, Benign Lesions, and Normal Skin Using Electric Impedance' IEEE Transactions on Biomedical Engineering, vol. 50, No. 8, Aug. 2003 (Year: 2003).*
"C-Therm—Simplifying Thermal Conductivity" C-Therm Technologies.
"C-Therm TCi Principles of Operation" C-Therm Technologies.
Bellhouse et al. "Thin-film Gauges for the Measurment of Velocity or Skin Friction in Air, Water or Blood," Journal of Scientific Instruments (Journal of Physics E). 2(1):1211-1213. (1968).
Bhattacharjee et al., "Material Recognition from Heat Transfer Given Varying Initial Conditions and Short-Duration Contact," Georgia Institute of Technology. (2015).
Bogdan "High-temperature, thin-film resistance thermometers for heat transfer measurement" NASA CR-26, 1964.
Fleszar. "Thermal Effusivity as a Non-Destructive Method to Characterize Thin Films," US Army Armament Research, Development and Engineering Center. (2003).
Ghorab et al., "Application of Thermal Effusivity as a Process Analytical Technology Tool for Monitoring and Control of the Roller Compaction Process," AAPS PharmSciTech. 8(1): Article 23. (2007).
Gustafsson. "Thermal Effusivity Measurements of Insulating Liquids Using Microsized Hot Strip Probes," Review of Scientific Instruments. 74: 4542. (2003).
Gustafsson. "Transient Hot Strip Technologies for Measuring Thermal Conductivity and Thermal Diffusivity," The Rigaku Journal. 4(½): 16-28. (1987).
Gustafsson. "Transient Plane Source Techniques for Thermal Conductivity and Thermal Diffusivity Measurements of Solid Materials," Review of Scientific Instruments. 62: 797. (1991).
Harris et al., "Measuring the Thermal Conductivity of Heat Transfer Fluids via the Modified Transient Plane Source," J. Therm. Anal. Calorim. 116: 1309-1314. (2014).
Log et al. "Transient Plane Source (TPS) Technique for Measuring Thermal Transport Properties of Building Materials" Fire and Materials. 19: 43-49. (1995).
Mathews et al., "Monitoring Blend Uniformity with Effusivity," Pharmaceutical Technology. pp. 80-84. (2002).
Mathis. "Transient Thermal Conductivity Measurements: Comparison of Destructive and Nondestructive Techniques," High Temperatures—High Pressures. 32: 321-327 (2000).
Maulard "Calibration method used at onera for hotshot and shock tube heat transfer transducers" Proc. 3rd Int. Congr. Instr. Aerosp. Simul. Facilities. IEEE/G-AES. May 1969. p. 96.
Mizzi "The Design of a Brushless drive to be operated with a Stirling Engine" Dissertation. University of Malta. 2014.
Rahman et al: "An improved thermal conductivity prediction model for fruits and vegetables as a function of temperature, water content and porosity", Journal of Food Engineering, Barking, Essex, GB, vol. 31, No. 2, Feb. 1, 1997, pp. 163-170, XP026748001.
Salmi. "Hot Disk Medical A Deeper Understanding." Scientific Discussions Presentation. (2010).

(56) References Cited

OTHER PUBLICATIONS

Sizov et al., "Thermal Conductivity Versus Depth Profiling of Inhomogeneous Materials Using the Hot Disc Technique," Review of Scientific Instruments. 87:074901.(2016).

Skold. "Detection of Damage in the Equine Hoof A possible new application for the Hot Disk Method?". MSC Thesis in Engineering Physics. (2017).

Uchiyama et al., "Evaluation of Risk and Benefit in Thermal Effusivity Sensor for Monitoring Lubrication Process in Pharmaceutical Product Manufacturing," Drug Development and Industrial Pharmacy. 40(8): 999-1004. (2014).

Zou et al., "Single-chip fabrication of integrated fluid systems (IFS)", Micro Electro Mechanical Systems, pp. 448-453 (1998).

* cited by examiner

NEEDLE PROBE, APPARATUS FOR SENSING COMPOSITIONAL INFORMATION, MEDICAL DRAIN, METHOD OF MEASURING A THERMAL PROPERTY, AND METHOD OF SENSING COMPOSITIONAL INFORMATION

CROSS-REFERENCE TO RELATED APPLICATIONS

This application is a divisional of U.S. patent application Ser. No. 16/156,943 filed on Oct. 10, 2018, which is a continuation of International Patent Application Number PCT/GB2017/051024 filed on Apr. 12, 2017, which claims priority to GB Patent Application Number 1606624.3 filed on Apr. 15, 2016, the contents of which are incorporated herein by reference in their entireties.

BACKGROUND OF THE INVENTION

The invention relates to sensing compositional information about material by measuring thermal properties of the material. The invention is particularly applicable to medical applications where a needle senses tissue for diagnostic or monitoring purposes and/or for assisting with surgical operations.

It is known to measure the properties of tissue in the human or animal body for various medical reasons. Existing methodologies can be expensive because they require complex processes. They can be time consuming where biopsies need to be sent away for analysis. It can be difficult for a surgeon to refer to information provided by existing techniques while performing surgery.

It can be difficult to detect when certain foodstuffs are no longer fresh enough to be suitable for sale or consumption, for example to meet food safety standards. This leads to food being thrown away earlier than necessary, leading to waste. It can also be difficult to detect when products (e.g. wine) that are sealed within a container (e.g. a corked bottle) have become damaged (e.g. by "corking") or have deteriorated (e.g. due to excessive age). The damage or deterioration is only detected when the product is finally unsealed, which can be inconvenient.

It is desirable to provide alternative techniques for measuring the properties of tissue in the human or animal body and/or for detecting information about freshness of foodstuffs or damage to sealed products.

BRIEF SUMMARY OF THE INVENTION

According to an aspect of the invention, there is provided a needle probe for sensing compositional information, comprising: a needle having a tip region; a resistive element attached to the needle at the tip region; a measurement system configured to 1) drive an electrical current through the resistive element to apply heating to the resistive element, and 2) measure an electrical response of the resistive element to the heating; and a processing unit configured to analyse the measured electrical response of the resistive element to the heating to determine compositional information about material in contact with the tip region.

The needle probe provides a sensitive and widely applicable alternative mode for obtaining compositional information about materials based on their thermal properties, for example the thermal product ($\sqrt{\rho c \kappa}$). The probe can be implemented using simple and cheap electronics in a compact, low power and safe unit. The needle probe is particularly applicable to medical applications where the needle can be inserted into target tissue of interest to determine information about the target tissue. The information may comprise information about the nature of the tissue (e.g. by distinguishing between cancerous tissue and normal tissue) and/or about processes occurring in the tissue which affect the chemical or structural composition of the tissue (e.g. due to inflammation, infection, etc.). The needle probe may make measurements within regions of tissue, at surfaces of tissue, and/or at interfaces (or "planes") between tissue of different types.

In an embodiment, the processing unit is configured to analyse the electrical response of the resistive element to detect either or both of the presence and concentration of metallic and/or magnetic (e.g. ferrous) nanoparticles in human or animal tissue adjacent to the tip region. Metallic nanoparticles can be introduced in such a way that they migrate preferentially to target tissue of interest (e.g. cancerous tissue). The marked effect on thermal properties caused by the metallic nanoparticles enables the needle probe to detect boundaries of the target tissue with high sensitivity. Magnetic (e.g. ferrous) nanoparticles may be introduced and their location controlled using an externally applied magnetic field. The magnetic nanoparticles may be attached to therapeutic agents (e.g. chemotherapy agents) designed for delayed release. The nanoparticles are localized using an externally applied magnetic field to a region of interest where the agent is released. The marked effect on thermal properties caused by the magnetic nanoparticles enables the concentration of the nanoparticles, and therefore of the therapeutic agent, to be estimated with high accuracy.

According to an alternative aspect there is provided an apparatus for sensing compositional information about tissue in the human or animal body, comprising: an elongate insertion device for insertion into the body, the insertion device comprising a first lumen; and the needle probe wherein the needle thereof is positioned within the first lumen such that the tip region can be brought into contact with tissue at a distal end of the insertion device.

This embodiment allows the needle probe to be brought to multiple regions within the body with minimally invasive surgery. In an embodiment of this type a tissue treatment device is also provided in a region adjacent to the distal end of the insertion device. The tissue treatment device may be configured to ablate tissue for example. This embodiment allows a surgeon to perform a treatment (e.g. removal of a cancerous tumour) using information provided by the needle probe to assist (e.g. by identifying the boundaries of a tumour to be removed). The tissue treatment device may be configured to inject an agent into tissue or to extract a substance from the tissue (e.g. a biological sample). This embodiment allows the injection or extraction process to be performed reliably at an optimal location.

According to an alternative aspect there is provided a medical drain for insertion to a target site in the human or animal body, comprising: a tube having a distal end and a proximal end, the tube being configured to allow material from the body to flow out of the body in use from the distal end at the target site to the proximal end outside of the body; a resistive element attached to the tube; a measurement system configured to 1) drive an electrical current through the resistive element to apply heating to the resistive element, and 2) measure an electrical response of the resistive element to the heating; and a processing unit configured to analyse the electrical response of the resistive element to determine compositional information about material in contact with the resistive element.

This embodiment allows information about the nature of material flowing in the tube to be obtained more reliably and/or more quickly, thereby allowing action to be taken more promptly and/or providing more accurate monitoring of a patient's health. This approach may allow patients to be discharged earlier from hospital than might otherwise be possible and/or allow action to be taken more promptly and/or more correctly in response to a change in the state of a patient. In the particular case where the medical drain is used to monitor the integrity of a repaired region of the bowel, leakage of faecal matter and/or any associated inflammation or infection can be detected more quickly and/or more reliably.

According to an alternative aspect there is provided a method of measuring a thermal property of a target portion of human or animal skin, comprising: bringing a resistive element of a probe element into contact with the target portion; driving an electrical current through the resistive element to apply heating to the resistive element; measuring an electrical response of the resistive element to the heating; and analysing the electrical response to determine information about the thermal property of the target portion.

Thus, a quick and convenient method is provided for measuring variations in the thermal properties of skin in different portions of skin. In an embodiment the method can be applied to detect abnormal moles.

According to an alternative aspect there is provided a method of sensing compositional information of a target material, comprising: providing a needle probe having a tip region and a resistive element attached to the tip region; bringing the tip region into contact with the target material; driving an electrical current through the resistive element to apply heating to the resistive element; measuring an electrical response of the resistive element to the heating; and analysing the electrical response to determine compositional information about the target material.

Thus, a quick and convenient method is provided for analysing compositional information about a target material. In an embodiment the target material comprises one or more of the following: a food item, wherein the tip region is inserted into the food item and the determined compositional information comprises information about the freshness of the food; a product (e.g. wine) sealed in a container (e.g. a wine bottle), wherein the tip region is inserted through a closure of the container (e.g. a cork) and the determined compositional information comprises information about the composition of the product. Freshness of food can be assessed quickly and objectively, reducing the risk of prematurely discarding food that is still suitable for consumption and/or enabling detection of food which is supposed to suitable for consumption but actually is not (e.g. because storage conditions have not been optimal). The state of sealed products such as wine can be assessed without unsealing the products, thereby reducing the risk of disappointment, inconvenience and/or financial consequence. Freshness can be assessed regularly or even continuously.

In an embodiment, packaging and/or a closure of a container (e.g. for food or drinks) may be provided in which the needle probe is permanently installed in the packaging or closure. The needle probe may be configured such that the tip region of the needle is exposed to an interior side of the packaging or closure, while electrical contacts are provided on the outside of the packaging or closure to allow the measurement system to make the necessary electrical contacts to the resistive element. Measurements of composition information of materials on the inside of the packaging or closure can thus be made conveniently simply by connecting the measurement system to the electrical contacts when required (it is not necessary additionally to insert the needle through the packaging, container or closure because the needle is already present in the appropriate position).

BRIEF DESCRIPTION OF THE SEVERAL VIEWS OF THE DRAWINGS

Embodiments of the invention will now be described, by way of example only, with reference to the accompanying drawings in which corresponding reference symbols indicate corresponding parts, and in which.

DETAILED DESCRIPTION OF THE INVENTION

The present inventors have recognised that the heat transfer characteristics of materials (e.g. thermal conductivity, $\kappa$, specific heat capacity, $c$, and quantities that depend on one or both of these properties) can depend sensitively on the composition (e.g. chemical or structural) of the materials. The thermal product, $\sqrt{\rho c \kappa}$, where $\rho$ is equal to the density, is often a heat transfer characteristic that is particularly sensitive to composition because it takes into account both $\kappa$ and $c$. Changes in either or both of $\kappa$ and $c$ will typically result in a change in $\sqrt{\rho c \kappa}$. Changes in relative concentrations of different components in a multi-component material can be detected particularly efficiently where the different components have very different thermal properties. For example, metallic or magnetic (e.g. ferrous) particles in water or human or animal tissue can be detected sensitively due to the fundamentally different thermal properties. At a temperature of 60° C., for example, the thermal conductivity of water is about 0.580 $Wm^{-1}K^{-1}$ compared to over 300 W/mK for metals such as gold, silver and copper.

The effect of the composition on the heat transfer characteristics of a material may not be derivable simply by summing the individual heat transfer characteristics of the components of the material. This is because multi-phase compositions may be present having complex thermal properties. However, for many compositions there will, overall, be a distinct correlation between the heat transfer characteristics and the composition that enables any changes in the composition (or differences relative to a reference) to be detected via measurements of the thermal properties.

The present inventors have recognised that detecting heat transfer characteristics of materials over time can provide a simple, effective and reliable way to detect changes in the composition of the materials.

Figures 1, 2, 3, 4:
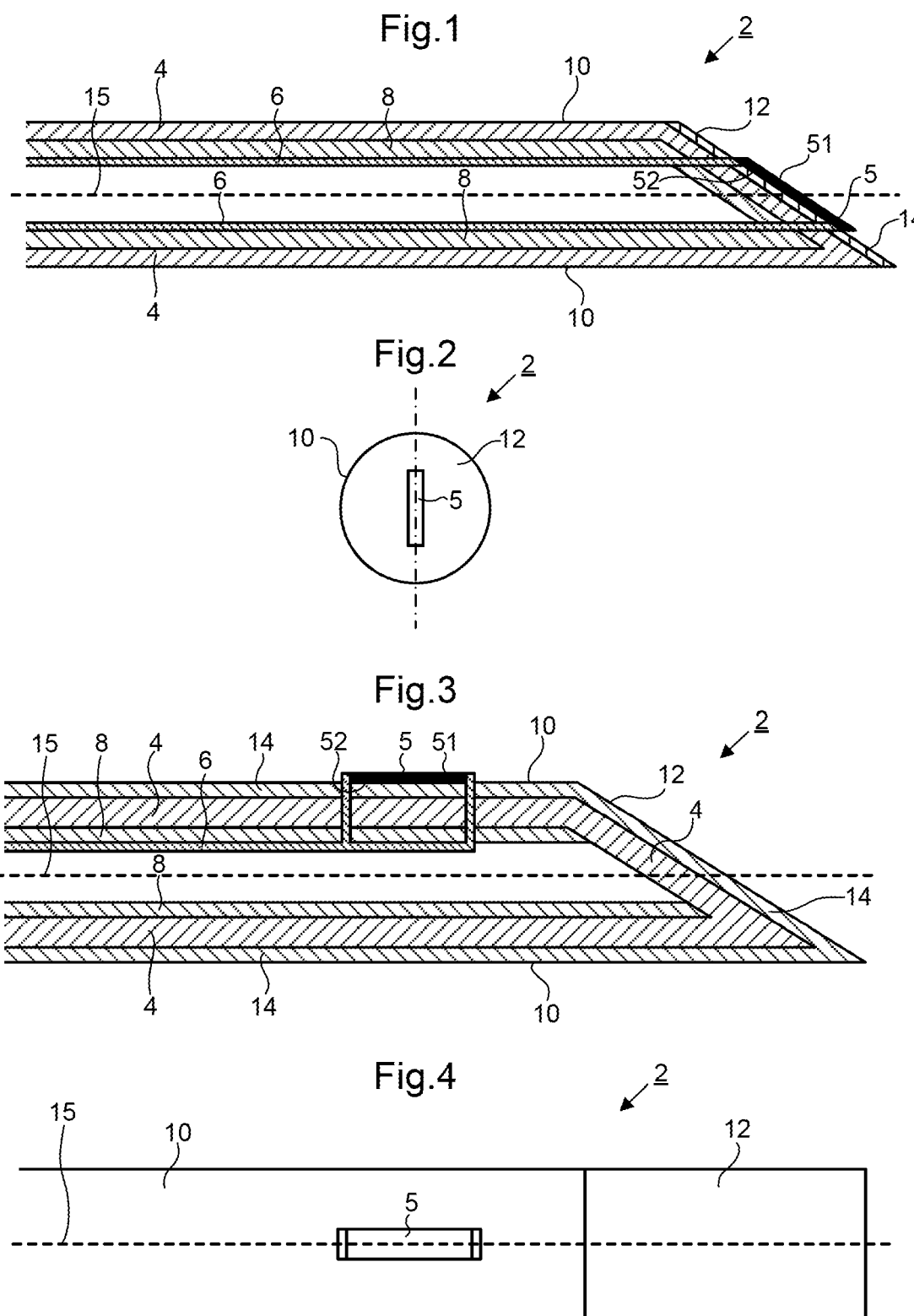
FIG. 1 is a schematic side sectional view of a tip region of a needle of a needle probe according to an embodiment.
FIG. 2 is a schematic end view of the tip region of FIG. 1.
FIG. 3 is a schematic side sectional view of a tip region of a needle of a needle probe according to an alternative embodiment.
FIG. 4 is a top view of the tip region of FIG. 3.

In an embodiment, examples of which are shown in FIGS. 1-8, there is provided a needle probe 30 for sensing compositional information. The needle probe 30 comprises a needle 2. The needle has a tip region. Particular examples of tip regions are shown in FIGS. 1 and 2, in FIGS. 3 and 4, and in FIG. 7. A resistive element 5 is attached to the needle 2 at the tip region.

In the context of the invention references to a needle are understood to mean an elongate element of relatively compact radial size, typically having a length to average cross-sectional width ratio of 5 or more, optionally 10 or more, optionally 20 or more. The average cross-sectional width is typically less than 10 mm, optionally less than 5 mm, optionally less than 2 mm, optionally less than 1 mm. The needle optionally has features on a distal end which allow the needle to penetrate into a material of interest, e.g. a progressive reduction in cross-sectional area, optionally converging to a point.

A measurement system 16 is configured to 1) drive an electrical current through the resistive element 5 to apply heating to the resistive element 5, and 2) measure an electrical response of the resistive element 5 to the heating. The electrical response may comprise a variation (curve) of voltage against time. The voltage may be related (e.g. proportional) to the resistance of the resistive element 5. The resistance may be related (e.g. proportional) to the temperature of the resistive element 5. A processing unit 18 is provided to analyse the measured electrical response of the resistive element 5 to the heating to determine compositional information about material in contact with the tip region. The variation in the temperature of the resistive element 5 with time will depend on the heat transfer characteristics of materials adjacent to the resistive element 5 because this will effect how efficiently heat will be conducted away from the resistive element 5. The heat transfer characteristics will depend on the chemical and/or structural composition of the material. The measurement of the electrical response therefore provides information about the chemical and/or structural composition of material adjacent to the tip region of the needle 2. The measurement system 16 and processing unit 18 may or may not be provided as separate units. In an embodiment the measurement system 16 and processing unit 18 are provided in a combined measurement/processing unit 22 (as shown schematically by a broken line box in FIG. 5). In an embodiment a handheld unit 24 is provided with a display and control interface 20 (e.g. touch screen display) for controlling the measurement/processing unit 22.

The measurement system 16 can be implemented in various different ways. One approach is described below in detail with reference to FIG. 11.

In an embodiment the processing unit 18 analyses the electrical response of the resistive element 5 to detect the presence or concentration of metallic nanoparticles in human or animal tissue adjacent to the tip region. Metallic nanoparticles have radically different thermal properties to native tissue and can be detected with a high level of sensitivity. Detection of metallic particles is demonstrated for example in the experimental results discussed below with reference to FIG. 12. This functionality may be particularly useful where the metallic nanoparticles are introduced in such a way that they migrate preferentially to tissue types of particular interest (e.g. cancerous tissue), enabling those tissue types or boundaries of those tissue types (e.g. boundaries between cancer tissue and normal tissue) to be detected using the needle probe 30.

In an embodiment the needle probe 30 is used to determine compositional information about a target material by inserting the distal tip region of the needle into the target material. The target material may comprise one or more of the following: a food item, wherein the tip region is inserted into the food item and the determined compositional information comprises information about the freshness of the food; a product (e.g. wine) sealed in a container (e.g. a wine bottle), wherein the tip region is inserted through a closure of the container (e.g. a cork) and the determined compositional information comprises information about the composition of the product. Optionally, the product (e.g. wine) can be sampled without unsealing the product. The needle probe 30 provides a novel and easy to use way for assessing whether food has gone off or whether a product such as wine in an unopened container is in good condition (e.g. whether a wine is "corked" or has deteriorated due to excessive age or oxidation). The inventors have recognised that chemical variations in composition caused by lack of freshness in food or damage to the product will lead to characteristic changes in the thermal properties of the food or product, which can conveniently be detected using the resistive element 5 of embodiments disclosed herein.

In an embodiment the tip region comprises a side surface 10. The side surface 10 encircles a longitudinal axis 15 of the needle 2. Where the needle 2 is substantially cylindrical the side surface 10 will be a cylindrical surface. The tip region further comprises an end surface 12. The end surface 12 is at an extreme distal end of the needle 2. The longitudinal axis passes through the end surface 12.

In an embodiment of this type the resistive element 5 is attached to the end surface 12. An example of such an embodiment is depicted in FIGS. 1 and 2. In this particular embodiment, the needle 2 is hollow and comprises a needle wall 4. An electrically insulating inner coating 8 is provided on an inner surface of the needle wall 4. The end surface 12 is formed by an electrically insulating outer coating 14 formed on the end surface 12. The resistive element 5 is formed directly on the end surface 12 or via a support material encapsulating the resistive element 5. In other embodiments the end surface 12 is an outer surface of the needle wall 4 and is therefore formed of the same material as the needle 2. This approach may be appropriate for example where the needle 2 is formed from an electrically insulating material such as a plastic and/or where the resistive element 5 is encapsulated in a support material that is electrically insulating. Leads 6 are provided for making electrical connections with the resistive element 5. The leads 6 may be electrically isolated from the needle wall 4 by the inner coating 8 and/or insulation around the leads 6 themselves. The implementation of the leads shown is just an example of what is possible. Various other ways may be used to provide the necessary electrical connections, including providing the leads as tracks outside of the needle 4, for example as tracks along the side surface 10. The tracks may optionally be provided in a recess along the side surface 10. The needle 2 is hollow in this example but this is not essential. In other embodiments, particularly where the leads 6 are provided outside of the needle 2, the needle 2 may be solid. Positioning the resistive element 5 on the end surface 12 facilitates positioning of the resistive element 5 adjacent to the material of interest, even when the material of interest is difficult to access. The inventors have recognised that this approach can be implemented effectively using extremely small resistive elements 5, thereby enabling placement of the resistive element 5 on end surfaces 12 of needles 2 even when the needles are of relatively small diameter (e.g. less than 10 mm diameter, optionally less than 5 mm diameter, optionally less than 2 mm diameter, optionally less than 1 mm diameter).

Alternatively or additionally the resistive element 5 may be attached to the side surface 10. An example of such an embodiment is depicted in FIGS. 3 and 4. In this particular embodiment, the needle 2 is hollow and comprises side walls 4, but may alternatively be solid. An electrically insulating outer coating 14 is formed around the whole tip region, thereby electrically insulating both the side surface 12 and the end surface 10 from the needle wall 4. In other embodiments, only the side surface 10 may be coated. The resistive element 5 is formed directly on the side surface 10 or via a support material encapsulating the resistive element 5. In other embodiments the side surface 10 is an outer surface of the needle wall 4 and is therefore formed of the same material as the needle 2. This approach may be appropriate for example where the needle 2 is formed from an electrically insulating material such as a plastic and/or where the resistive element 5 is encapsulated in a support material that is electrically insulating. Positioning the resistive element 5 on the side surface 10 allows the resistive element 5 to be longer. Allowing the resistive element 5 to be longer may facilitate manufacture and/or improve the robustness of the resistive element 5 for a given overall resistance (the resistive element 5 can be made thicker for the same resistance).

In an embodiment the resistive element 5 is elongate and an axis of elongation is substantially aligned with a longitudinal axis of the needle 2. This configuration allows the resistive element 5 to be relatively longer. In an alternative embodiment, the resistive element 5 is configured to encircle the longitudinal axis of the needle 2, optionally wrapping around the axis in a helix. This approach allows the resistive element 5 to sample material through a range of angles round the needle 2. This approach also allows the resistive element 5 to occupy only a small length of the needle in the longitudinal direction while still allowing the resistive element 5 to be relatively long. Longitudinally localising the resistive element 5 in this manner may increase the spatial resolution of the needle probe in the longitudinal direction, allowing changes in composition along the longitudinal direction to be distinguished with higher spatial resolution.

In typical embodiments the resistive element 5 is metallic. In such embodiments, contact between the resistive element 5 and the material to be sensed will not typically result in a significant reduction in the resistance of the electrical path from one end of the resistive element 5 to the other end of the resistive element 5. The resistivity of the resistive element 5 is typically much lower than the resistivity of the material to be sensed.

In an embodiment the resistive element 5 is mounted on a substrate in such a way that at least 10% of the surface area of the resistive element 5 is in contact with the substrate, optionally via a support material encapsulating the resistive element 5 (e.g. a thin film of electrically insulating material), optionally more than 30%, optionally around 50%. In an embodiment the resistive element 5 is a thin film resistive element (e.g. thin film resistance thermometer). In an embodiment the resistive element 5 comprises a thin film of platinum mounted on a substrate.

In an embodiment the resistive element 5 is a thin film resistive element having a first surface 51 configured to face towards the material to be sensed and a second surface 52 facing towards the substrate. It is understood that the first and second surfaces 51,52 are the large surfaces of the thin film (and do not include any of the very thin side surfaces). In an embodiment no portion of the material being sensed is present between the second surface 52 and the substrate.

In the example shown in FIGS. 1 and 2, the substrate is the combination of the portions of the outer coating 14, the needle wall 4 and the inner coating 8 that are directly adjacent to the resistive element 5, together with any portion of a support material encapsulating the resistive element 5 that is positioned between the resistive element 5 and the relevant portions of the other layers 14, 4, 8. In the example shown in FIGS. 3 and 4, the substrate is the combination of the portions of the outer insulating coating 14 and the needle wall 4 that are directly adjacent to the resistive element 5, together with any portion of a support material encapsulating the resistive element 5 that is positioned between the resistive element and the relevant portions of the other layers 14, 4.

The presence of the substrate allows relatively large currents to be applied to the resistive element 5 without the resistive element 5 overheating, which could damage the resistive element 5 and/or material that is in contact with the resistive element 5.

In an embodiment a pulse of heating may be applied. A response to the pulse of heating may be compared with the response to the same pulse applied to a reference material (which may for example be the same material being sensed at a previous time). The size of the response, the variation of the response as a function of time, or various other aspects of the response may be considered. Any deviation from the response to the same pulse applied to the reference material may indicate a change in the composition of the sample which is of interest, including a change in the chemical or structural composition of the material. The nature of the heating may be varied to tune the sensitivity of the detection process. The nature of the heating may be varied for example by changing the shape, size, duration or repetition rate of a heating pulse or series of pulses, for example.

Figure 12:
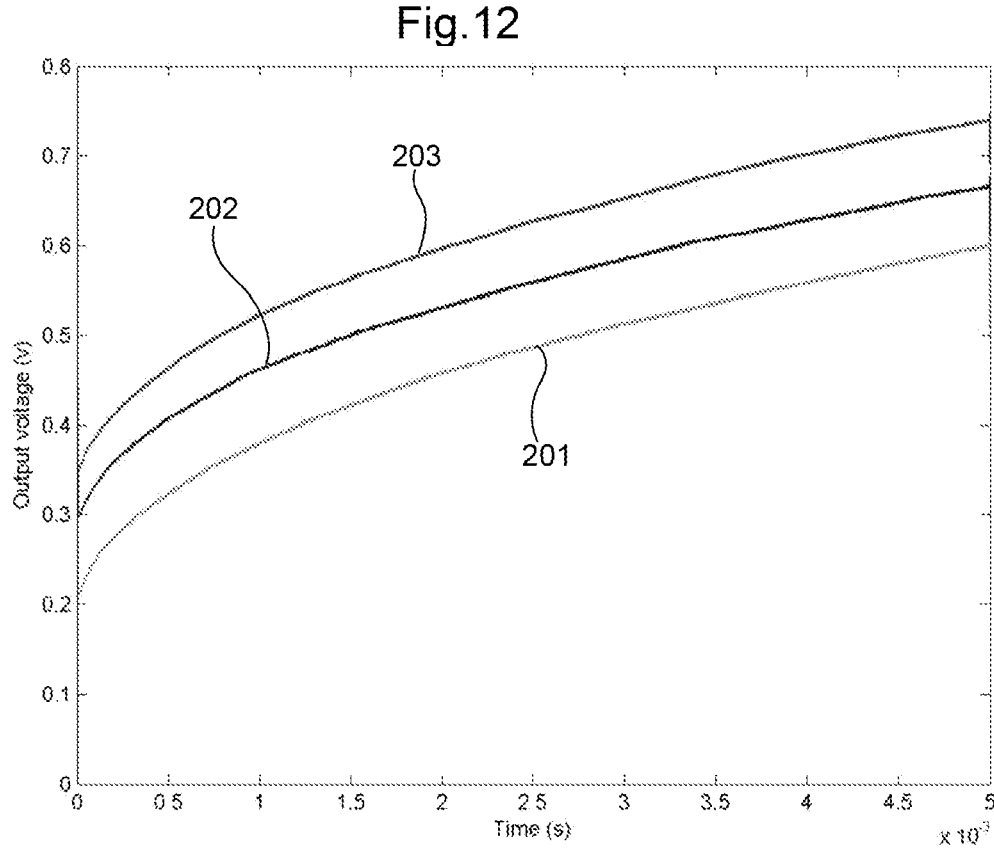
FIG. 12 is a graph showing responses of a platinum thin film resistive element to a heating pulse when in contact with three different liquids.

FIG. 12 depicts example data obtained using an embodiment in which the resistive element 5 comprises a thin film formed from platinum mounted on a machinable glass-ceramic substrate. The vertical axis shows an output voltage from the resistive element 5 during application of a heating pulse of constant electrical current (corresponding to 5V through a resistance of about 50 Ohms) to the resistive element 5. The vertical axis is proportional to the resistance of the resistive element 5, which in turn varies in a predetermined way as a function of the temperature of the resistive element 5. The horizontal axis measures time from 0 to 5 ms, which in this case corresponds to the duration of the heating pulse. The resistive element 5 was mounted flush against the substrate, so in this particular example approximately 50% of the surface area of the platinum film was exposed to the liquid being tested. The three curves shown in FIG. 12 illustrate respectively how the resistance (and thus temperature) of the resistive element 5 changed as a function of time during application of the heating pulse when the resistive element 5 was in contact with each of three different formulations of liquid. Curve 201 corresponds to the case where the liquid comprised oil only. Curve 202 corresponds to the case where the liquid comprised a mixture of oil and water. Curve 203 corresponds to the case where the liquid comprised a mixture of oil and small copper particles. As can be seen, the heights of the three curves 201-203 are markedly different despite the fact that identical heating pulses were applied in each case. The differences between the three curves 201-203 arise because of the different heat transfer characteristics of the liquids in each case.

The measurement system 16 may be configured to deliver power to the resistive element 5 by driving an electrical current through the resistive element 5 at the same time as measuring the resistance (and therefore temperature, where a calibration is available) of the resistive element 5. If the resistive element 5 is made from platinum, for example, a very linear relationship between temperature and resistance is known.

The change in resistance/temperature of the resistive element 5 caused by the heating will depend on the ability of material in contact with the resistive element 5 to carry the heat away and therefore on the heat transfer characteristics of the material. If the heat transfer characteristics of the material are different relative to a reference, for example changed due to a change in composition, this will be detectable as a deviation in the relationship between the amount of heat supplied and the resulting change in resistance/temperature of the resistive element 5 from what would be expected for the reference. Example circuitry for a measurement system 16 configured to perform such measurements is shown in FIG. 11.

Figure 11:
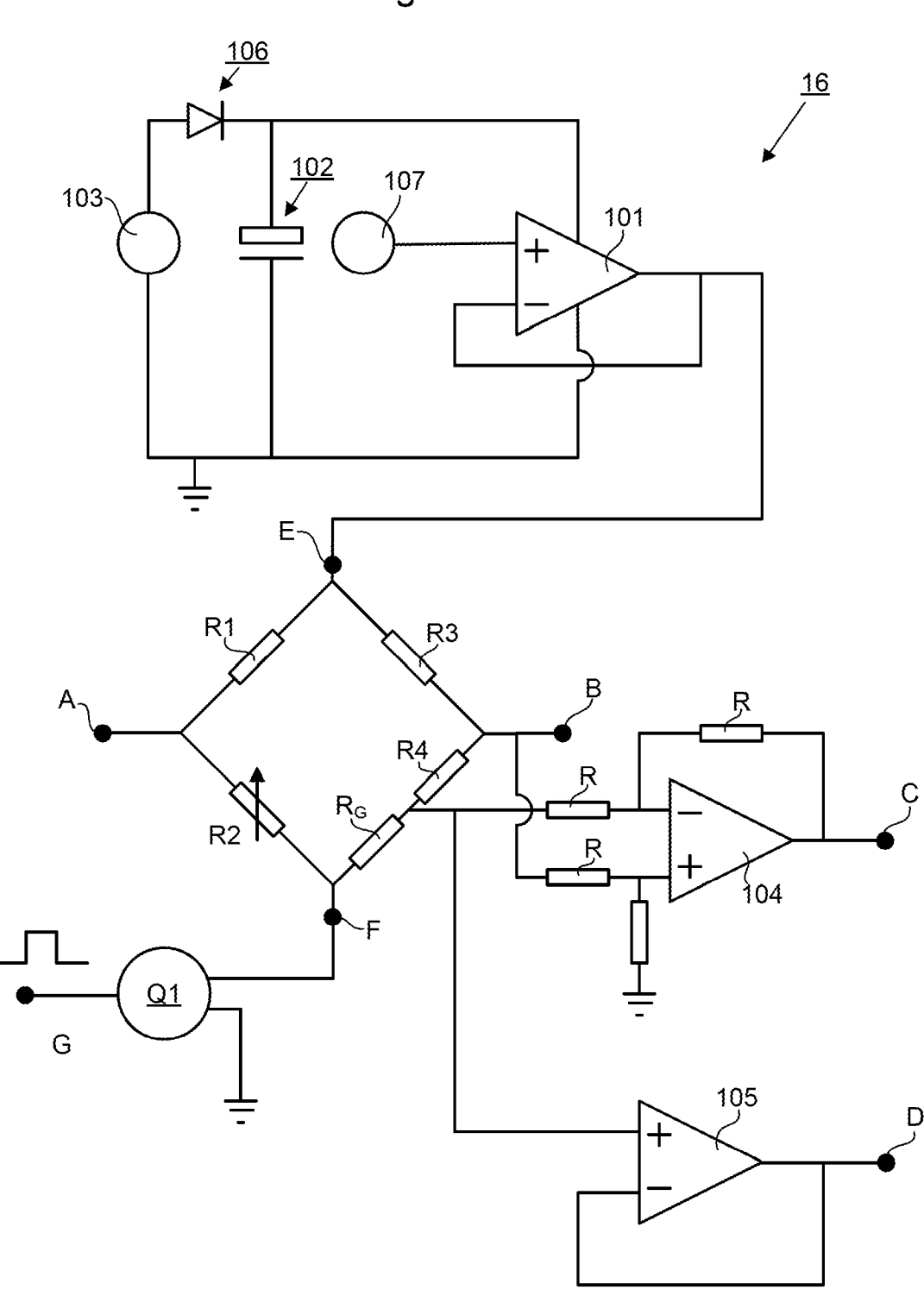
FIG. 11 depicts example circuitry for implementing a measurement system of a needle probe.

The following elements are shown in FIG. 11:
101 Power amplifier (e.g. about 10 A RATED)
102 Charge store (e.g. about 40,000 µF)
103 Power supply (e.g. about 30V DC)
104 Differential amplifier for I
105 Buffer amplifier for V
R1+R2 Bridge balance
R3+$R_G$ Active bridge half
Q1 Power switch (e.g. fast, low resistance MOSFET)
C Output of current I
D Output of voltage V
E High side of bridge
F Low side of bridge
G Signal pulse control
R4 Current sense shunt (resistance) (e.g. 20 mΩ)
A+B Diagnostic differential signal outputs for development
106 Diode rectifier
107 Voltage reference A voltage generated by voltage supply 103 is fed through a rectifier diode 106 to charge a high capacity storage 102. The storage 102 provides a high current power source to the power amplifier 101. A voltage reference 107 sets a high side voltage presented at E.

A bridge is created between the points A, E, B and F. In an example, R3 and $R_G$ are about 1.0 Ohms, and R1 and R2 are about 470 Ohms. A power switch device Q1 is provided to rapidly bring point F to ground under a signal pulse at G. The circuit enables a steady bridge voltage to be maintained without demanding a high gain bandwidth from the power amplifier 101. The power amplifier 101 needs only to maintain a DC level. High energy pulses of precise timing are made possible using a fast MOSFET power switch for Q1 at the low side of the bridge.

When the bridge is energised the differential voltage points (A & B) will provide a voltage corresponding to the Ohmic resistance change of the gauge element $R_G$ (e.g. the resistive element 5). The other resistors in the bridge are chosen to have a very low parts-per-million (ppm) change in resistance with temperature. Therefore observed bridge voltages are only a function of the gauge $R_G$.

For precise measurements of heat transfer to the resistive element 5, and from the resistive element 5 to material in contact the resistive element 5, it is desirable to measure the voltage V and current I across the element 60. The current is determined from the output of the circuit at C. The voltage is determined from the output of the circuit at D. Thus the energy input and the corresponding rise in temperature can be determined and the heat transfer function to the material in contact with the resistive element 5 can be computed.

The total energy and energy rate can be controlled by varying the reference voltage 107 and the pulse duration at G. In a typical embodiment, a pulse will last a few milliseconds and will not be repeated for several hundreds of milliseconds.

The circuit allows a modest power source to store energy to deliver very high energy density pulses. Electronic controls will activate the power level and pulses duration whilst reading the voltage signals at C and D. The electronic controls may be provided by the measurement system 54 or the processing unit 4 (or both).

In an embodiment, fast ADC to storage in computer memory will be employed leaving time to compute the heat transfer data from which quantitative measurements can be performed and compared to calibrated lookup tables to provide qualitative assessments of the contamination characteristics of the sample (e.g. tissue) being tested. This functionality may for example be performed in the processing unit 18.

Figure 13:
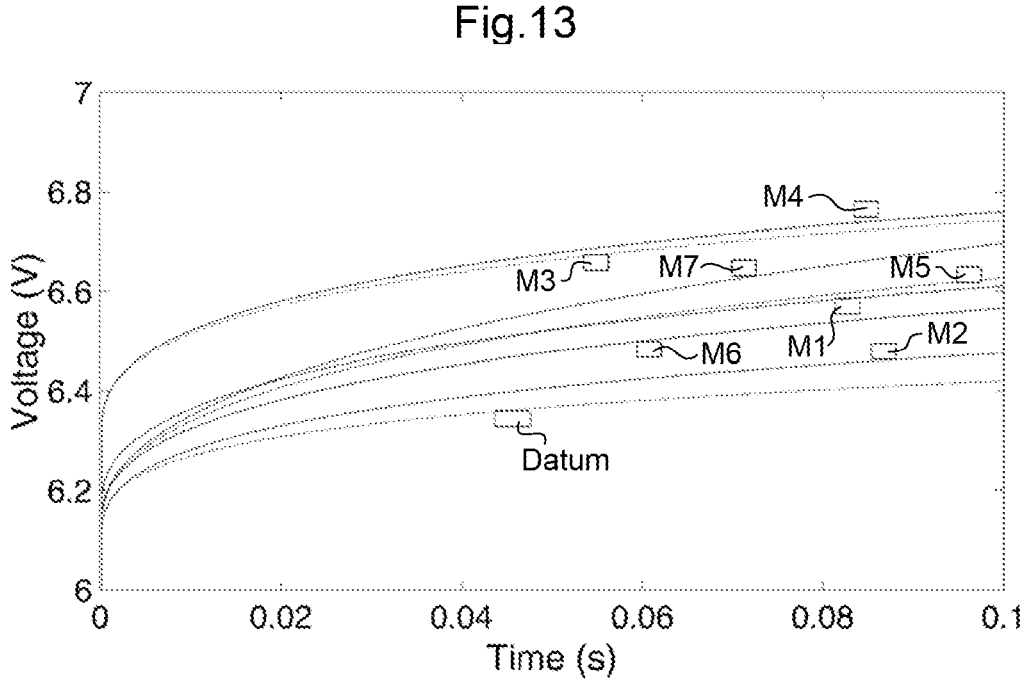
FIG. 13 is a graph showing changes of resistance with time during heating of a resistive element in contact with different solid samples.

FIG. 13 show representative data showing the result of applying a heating pulse to a resistive element 5 comprising a thin film encapsulated by a support material when the material being sensed comprises a variety of different solid objects. The curve for a reference solid object is labelled "Datum". Curves for other solid objects of nominally identical composition are marked M1-M7. In this particular example the solid objects are samples of fine grained rock. The vertical axis shows an output voltage from the resistive element 5 during application of the heating pulse. The vertical axis is proportional to the resistance of the resistive element 5, which in turn varies in a predetermined way as a function of the temperature of the resistive element 5. The horizontal axis measures a time interval spanning application of the heating pulse. FIG. 13 demonstrates that even for solid samples of nominally identical composition, small changes in actual composition lead to detectable differences in the response of the resistive element 5 to a heating pulse, thereby enabling detection of deviations of the samples from a reference ("Datum").

In embodiments where the resistive element 5 is separated from the material being sensed by a support material or other material, the electrical current should be applied for a period (e.g. pulse length) which is long enough for the heat generated to pass significantly into the material being sensed. If the pulse length is too short the heating will only sample the support material or other material and provide information about the thermal properties of the support material or other material, which may not be of interest. This is why the pulse length (0.1 s) in the example of FIG. 13 (where the resistive element is encapsulated by a support material) is much longer than the pulse lengths used in the example of FIG. 12. The fact that the heat generated at the resistive element 5 samples different layers sequentially can be used to obtain information about different layers of a sample in a single measurement. Variation of the resistance of the resistive element in different time windows can be attributed to different layers (earlier time windows corresponding to shallower layers than deeper time windows). This provides a convenient way of obtaining information about the thermal properties of a sample selectively at different depths within the sample.

Figures 5, 6, 7:
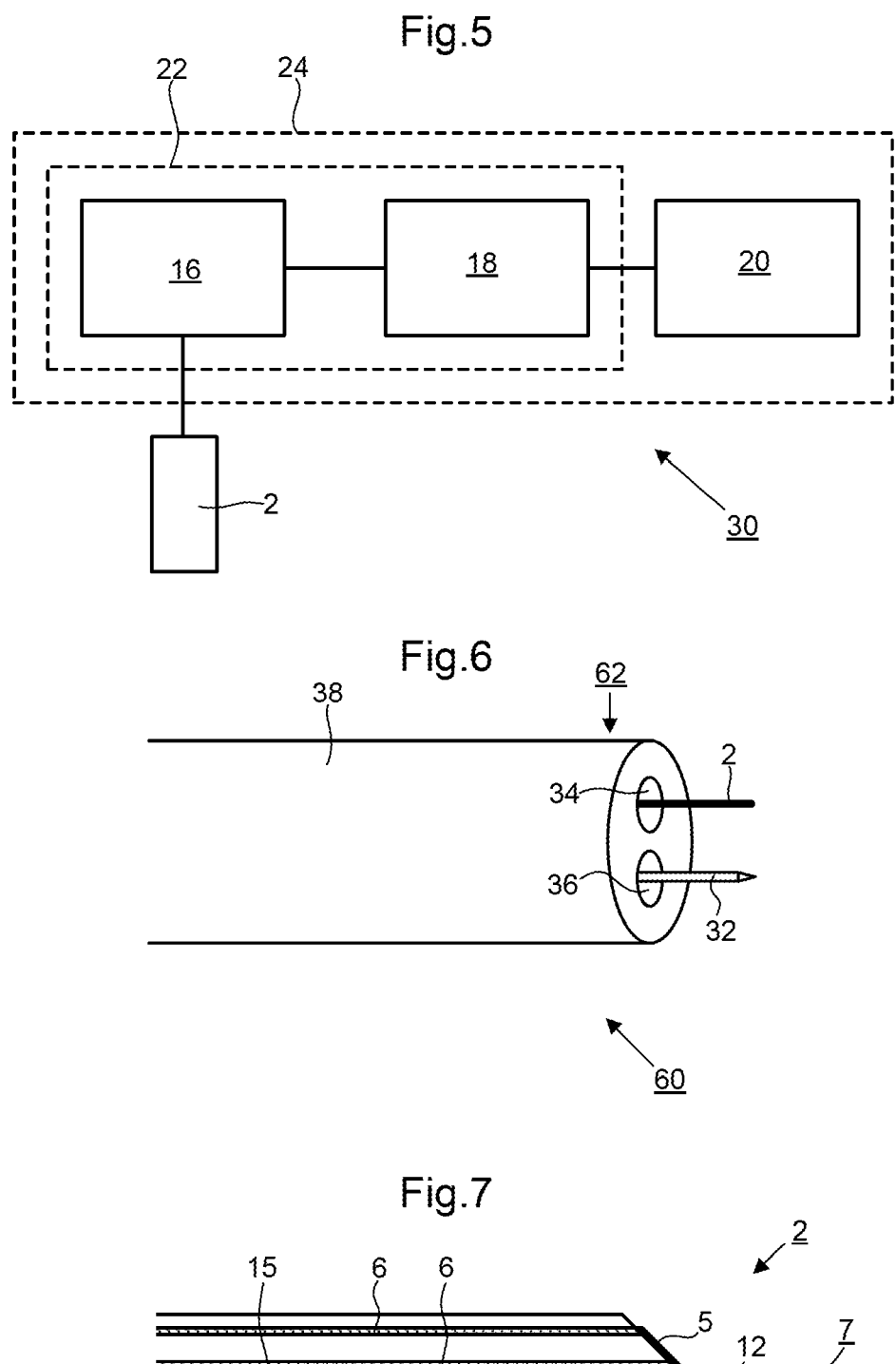
FIG. 5 schematically depicts a needle probe according to an embodiment.
FIG. 6 schematically depicts an apparatus for sensing compositional information in the human or animal body.
FIG. 7 is a schematic side sectional view of a tip region of a needle having an internal lumen for injection or extraction.

In an embodiment, an example of which is depicted in FIG. 6, there is provided an apparatus 60 for sensing compositional information about tissue in the human or animal body. The apparatus 60 comprises an elongate insertion device 38. The elongate insertion device 38 may comprise a catheter or endoscope for example. The elongate insertion device 38 may be configured to be inserted to a target tissue of interest in a variety of different ways. For example, one or more natural orifices or lumens such as are provided by the vascular system, digestive system and respiratory system (for example) may be used. Alternatively, the elongate insertion device 38 may traverse tissue, for example the abdominal wall, taking the form for example of a laparoscopic port or sheath.

The elongate insertion device 38 comprises a first lumen 34. A needle 2 of a needle probe according to an embodiment is positioned with the first lumen 34 such that the tip region can be brought into contact with tissue at a distal end 62 of the insertion device 38. For example, the needle 2 may be configured so that it can be fully within the first lumen 34 during an insertion process of the insertion device 38 and subsequently advanced longitudinally so that the distal tip protrudes beyond the distal end 62 of the insertion device (as shown for example in the arrangement of FIG. 6).

In an embodiment the apparatus 60 further comprises a tissue treatment device 32 for treating tissue in a region adjacent to the distal end 62 of the insertion device 38. In an embodiment the tissue treatment device 32 is configured to ablate tissue. The tissue treatment device 32 may access the region adjacent to the distal end 62 through the first lumen 34 (not shown) or through a second lumen 36 (shown in FIG. 6).

The apparatus 60 conveniently provides a surgeon with the possibility of evaluating a nature of tissue using the needle probe during an operation on tissue using the tissue treatment device 32. The apparatus 60 provides the surgeon with additional information about the nature of the tissue, thereby enabling the operation to be performed more reliably or accurately. For example, where the operation involves removal of suspect or cancerous tissue, the apparatus 60 may assist the surgeon in identifying a boundary between the suspect or cancerous tissue and non-suspect or normal tissue. This approach may be particularly effective for example where metallic nanoparticles that migrate preferentially to tissue types of particular interest are used as these may be detected by the needle probe with particularly high sensitivity. The apparatus 60 may be effective even in the absence of metallic nanoparticles due to differences in the tissue structure (e.g. density) or composition (e.g. due to differences in metabolism) that have an effect on the thermal properties of the tissues and thereby enable the needle probe to distinguish the tissue. In an embodiment the surgeon may compare measurements made by the needle probe in tissue which is known to be normal with measurement made by the needle probe in tissue which is to be evaluated, using otherwise identical conditions. When the measurement differs from the measurement made on normal tissue by more than a predetermined reference amount it may be concluded that the tissue is not normal (e.g. it is cancerous) and appropriate surgical action or treatment can then be applied.

The needle probe 30 may also be used to detect magnetic (e.g. ferrous nanoparticles) in tissue. Magnetic nanoparticles may be associated with therapeutic agents (e.g. connected to structures containing the therapeutic agents), for example chemotherapy agents, and guided to a location of interest using an externally applied magnetic field. The needle probe 30 can detect the concentration of the magnetic nanoparticles with high accuracy, thereby enabling the dose being administered to be estimated with high accuracy.

Metallic and magnetic nanoparticles have thermal properties which are radically different to those of tissue, and are therefore particularly easily detectable by the needle probe. As an illustrative example, the thermal product $\sqrt{\rho c \kappa}$ of gold is about 28000 $Ws^{1/2}K^{-1}m^{-2}$ whereas a typical thermal product of tissue is in the region of 1300 $Ws^{1/2}K^{-1}m^{-2}$.

Figures 8, 9:
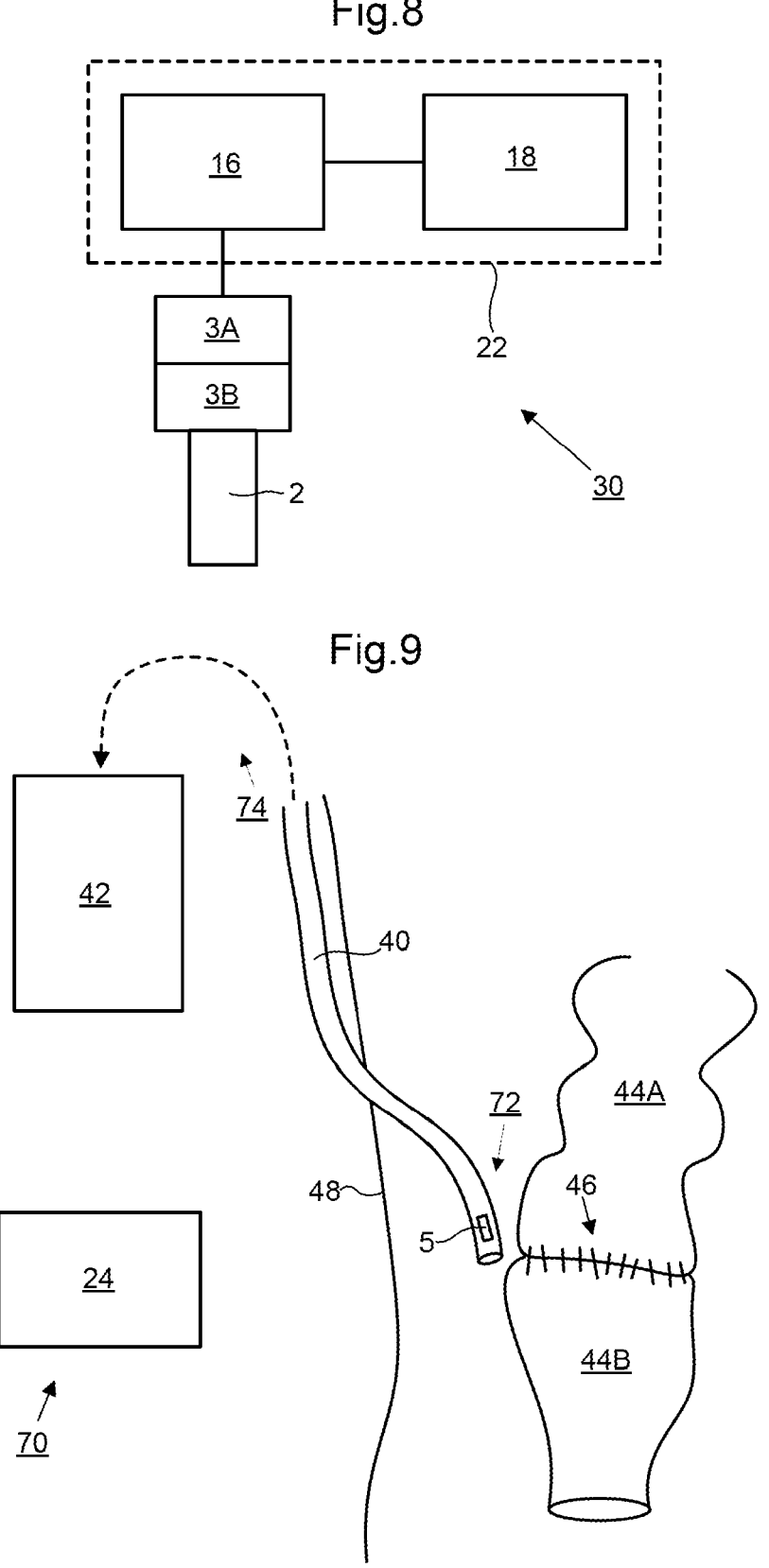
FIG. 8 schematically depicts a needle probe having an injection device or substance extraction device.
FIG. 9 schematically depicts a medical drain.

In an embodiment, an example of which is shown in FIG. 7, the needle 2 comprises an internal lumen 7. The internal lumen 7 is configured to allow injection of an agent (e.g. therapeutic agent) to a target site through the needle or extraction of a substance (e.g. biological sample) from the target site through the needle 2. As shown in FIG. 8, the needle probe 30 may further comprise an injection device 3A, an extraction device 3B, or both. The injection device 3A is configured to inject an agent through the needle 2. The injection device 3A may comprise, for example, a pump for driving the agent through the needle 2 and a reservoir for containing the agent prior to delivery. The extraction device 3B is configured to extract a substance through the needle 2. The extraction device 3B may comprise, for example, a pump for pulling the substance through the needle 2 and a container for receiving the substance or a port for outputting the extracted substance.

The ability of the needle probe to detect the composition of material in contact with the tip region provides the medical practitioner seeking to inject an agent or extract a substance with valuable information about where the tip is located. The medical practitioner can insert the needle with less risk of damage and inject or extract material more reliably. The risk of damage or sub-optimally effective treatment caused by inserting the tip too far and/or injecting or extracting material from the wrong location can be reduced or eliminated. Where the needle needs to be inserted through different layers of tissue, changes in the composition of material adjacent to the tip region can be detected as the needle is advanced, thereby providing an indication when each layer of tissue is traversed. For example, in the case where the needle probe is used to administer an anaesthetic, for example in a spinal epidural block or a tap block, the processing unit can indicate when the tip region is located so as to delivery the anaesthetic in the most effective manner. In the case where the needle probe is used to extract a biological sample, for example spinal fluid, the processing unit can indicate when the tip region is located within the appropriate tissue. The needle probe can also provide diagnostic information itself while located in the region where the biological sample is to be collected (e.g. by detecting abnormal thermal properties of tissue which may be indicative of infection or abnormal presence of red blood cells).

In a further embodiment, an example of which is shown schematically in FIG. 9, there is provided a medical drain 70. The medical drain 70 is configured to be inserted in use to a target site in the human or animal body 48. The medical drain 70 comprises a tube 40. The tube 40 has a distal end 72 and a proximal end 74. The tube 40 is configured to be positioned to allow material from the body to flow out of the body in use from the distal end 72 at the target site to the proximal end 74 outside of the body. The tube 40 may be inserted for example so that the distal end 72 is positioned in a region adjacent to a repaired portion 46 of bowel. The repaired portion 46 may be formed after an operation to remove a section of bowel for example and consists of a region where parts 44A and 44B either side of the cut are connected together. It is common practice in this medical situation to insert a medical drain during a period after the operation to allow fluids generated in the region of the operation to be drained away from the body. A risk with this kind of operation is that the repaired portion 46 does not remain fully intact and faecal matter leaks out of the bowel at the repaired portion 46. This event can lead to serious medical complications and needs to be detected quickly. Existing approaches do not allow this detection to take place optimally. For example it is not quickly apparent from material leaving the medical drain that such a leak has occurred due to the delay associated with material moving down the medical drain and/or the need for detailed analysis of the fluids to be carried out, particularly in the early stages of such a leak, to diagnose the event reliably.

Embodiments of the invention address this situation and other analogous situations by using a resistive element 5 to detect changes in the nature of material in contact with the resistive element 5 at a distal end 72 of the tube 40.

In an embodiment the resistive element 5 is attached to the tube 40. As in the embodiments discussed above the measurement system 16 (not shown) is configured to: 1) drive an electrical current through the resistive element 5 to apply heating to the resistive element 5, and 2) measure an electrical response of the resistive element 5 to the heating. As in the embodiments discussed above a processing unit 18 (not shown) is provided. The processing unit 18 analyses the electrical response of the resistive element 5 to determine compositional information about material in contact with the resistive element 5.

In an embodiment the resistive element 5 is positioned so as to be in thermal contact with material flowing through the tube 40. The resistive element 5 may be positioned on an inside surface of the tube 40 or in a region directly adjacent to an opening in the distal end 72 of the tube 40 through which material flowing through the tube 40 initially enters the tube 40.

In an embodiment the processing unit 18 determines the compositional information a plurality of times and detects a change in the compositional information indicative of a medically relevant event at the distal end 72 of the tube 40. As mentioned above the medically relevant event may comprise a leak of faecal matter from a repaired portion 46 of bowel. In this and other medical situations the medically relevant event may additionally or alternatively comprise one or both of inflammation and infection.

In other embodiments, the compositional information of material flowing through the tube may be measured outside of the body. Alternatively or additionally, a needle probe 30 may be inserted independently of the drain 70, or in a situation where the drain 70 is not even provided, and used to measure the composition of matter in the region of the target site. Such an arrangement may allow a patient to return home from hospital earlier without compromising safety. Data obtained from the needle probe 30 may be sent to the hospital via a network to allow the condition of the patient to be monitored remotely. If the needle probe 30 detects a change in thermal properties indicative of a potential problem the patient can be contacted and returned to hospital for further evaluation and/or treatment or surgery.

Information provided by the needle probe 30 may be used in combination with other information about the patient (e.g. vital signs, white blood cell count, etc.) to improve the accuracy of diagnoses.

Figure 10:
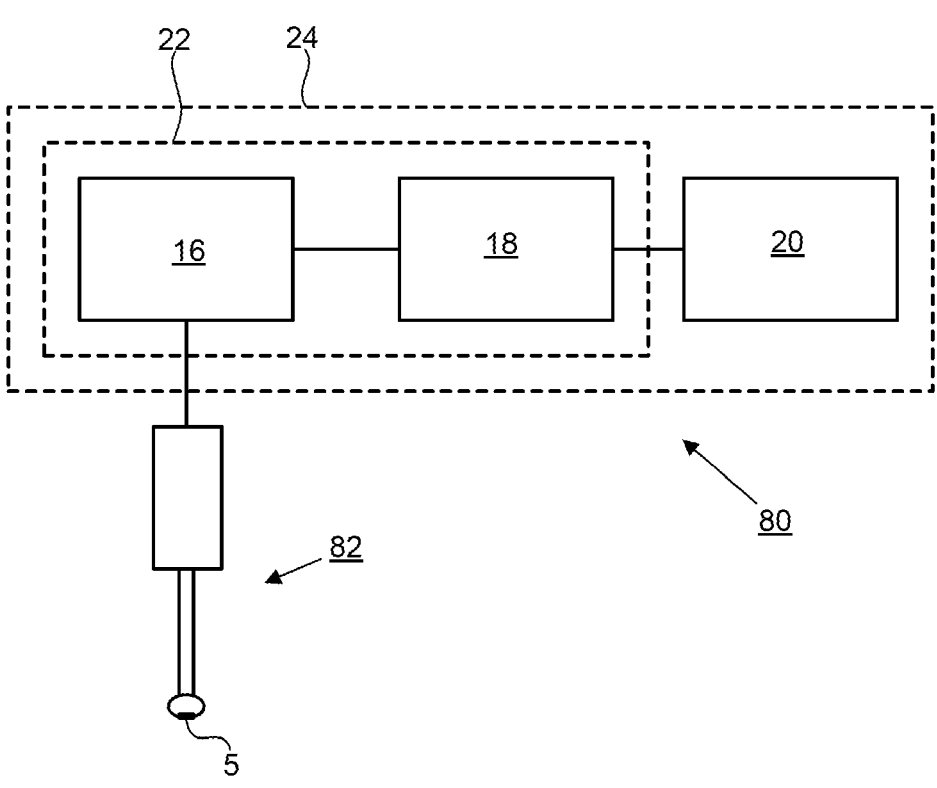
FIG. 10 schematically depicts a probe element for measuring a thermal property of a target portion of human or animal skin.

In an alternative embodiment, a method of measuring a thermal property of a target portion of human or animal skin is provided. The method comprises bringing a resistive element 5 of a probe element 80 into contact with the target portion. The probe element 80 may be configured in the same manner as in any of the embodiments of the needle probe discussed above except that the resistive element 5 is attached to a probe 82 that is not necessarily a needle 2. An example configuration is shown in FIG. 10. A measurement system 16 and processing unit 18 may be provided as described above with reference to FIG. 5. According to the method an electrical current is driven through the resistive element 5 to apply heating to the resistive element 5. The measurement system 16 and processing unit 18 may or may not be provided as separate units. In an embodiment the measurement system 16 and processing unit 18 are provided in a combined measurement/processing unit 22 (as shown schematically by a broken line box in FIGS. 5 and 8). In an embodiment a handheld unit 24 is provided with a display and control interface 20 (e.g. touch screen display) for controlling the measurement/processing unit 22. An electrical response of the resistive element 5 to the heating is measured. The electrical response is analysed to determine information about the thermal property of the target portion.

In an embodiment the information about the thermal property of the target portion is obtained at a plurality of different times in order to detect a change in the composition of the target portion over time. For example, in the case where the target portion is a mole or other irregularity on the skin, the method may be used to detect changes which may be indicative that the mole or other irregularity should be investigated further by a medical professional.

In an embodiment the information about the thermal property is obtained for a plurality of target portions in order to detect a difference in the thermal property in one target portion in comparison to one or more other target portions. In an embodiment the target portion and the one or more other target portions each comprise a different mole or other irregularity on the skin. The method can be used to detect when the composition of one mole is different to other moles, which may be indicative that the mole should be investigated further by a medical professional.

Figure 14:
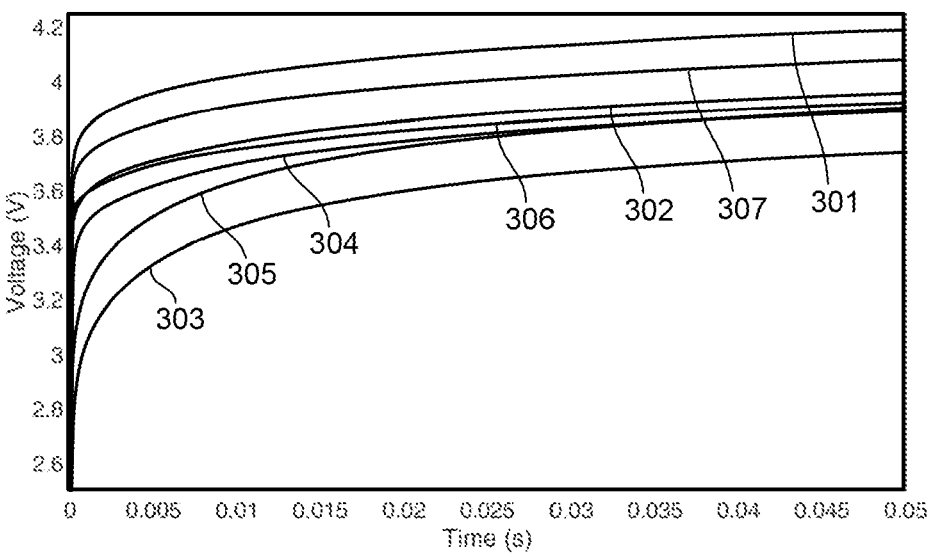
FIG. 14 is a graph showing changes of resistance with time during heating of a resistive element in contact with different layers of a sample of porcine belly.

A needle probe 30 according to an embodiment was tested by progressively inserting the needle probe 30 through different layers of dead porcine tissue (a piece of pork belly) at 17.5 degrees C. Results were obtained in near real time and were reproducible. Example data is depicted in FIG. 14, which shows a variation of a measured voltage across the resistive element 5 with time during a heating pulse. The shape of the curves is broadly the same as the curves shown in FIGS. 12 and 13 due to the dependence on thermal product. Differences in thermal product between different types of tissue leads to characteristic differences in the behaviour of the measured voltage against time, demonstrating that the needle probe 30 can distinguish sensitively between different types of tissue. The different curves are marked as follows: skin (301); fat (302); muscle (303); fascia (304); deep muscle (305); deep fat (306); and bone (307).

Figure 15:
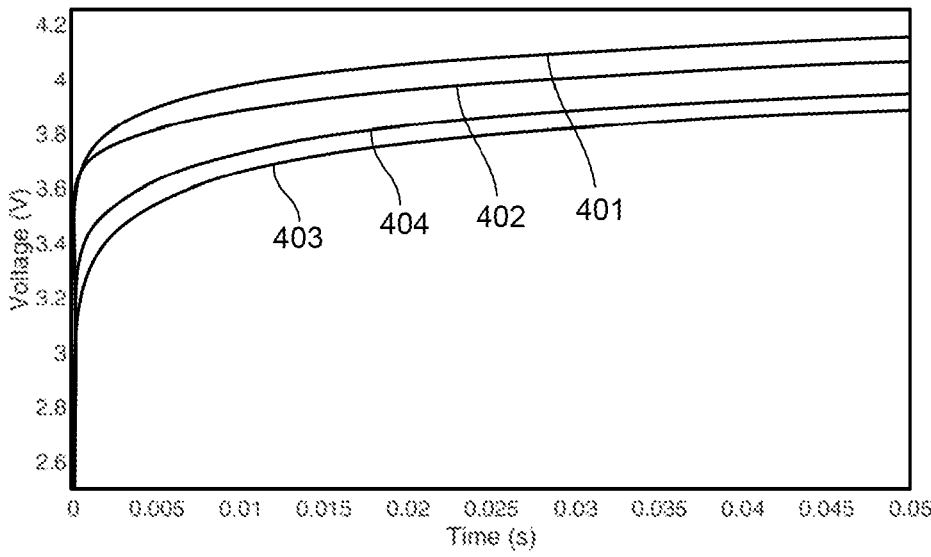
FIG. 15 is a graph showing changes of resistance with time during heating of a resistive element in contact with different layers of a sample of porcine thigh.

FIG. 15 depicts corresponding data for a case where the needle probe 30 was inserted into porcine thigh tissue at 17.5 degrees C. The different curves are marked as follows: skin (401); fat (402); muscle (403) and fascia (404).

The data of FIGS. 14 and 15 demonstrate how the needle probe 30 can be used to monitor a position of a tip of the needle as it is inserted through layered tissue structures. This may provide useful feedback in a variety of surgical (and non-surgical) situations. For example, the needle probe 30 may be used to facilitate epidural injections, where correct judgement of the optimal injection point by manual "feel" is known to be prone to error. The needle probe 30 can provide greater reliability and/or reduce the need for extensive manual experience in this context.

Figure 16:
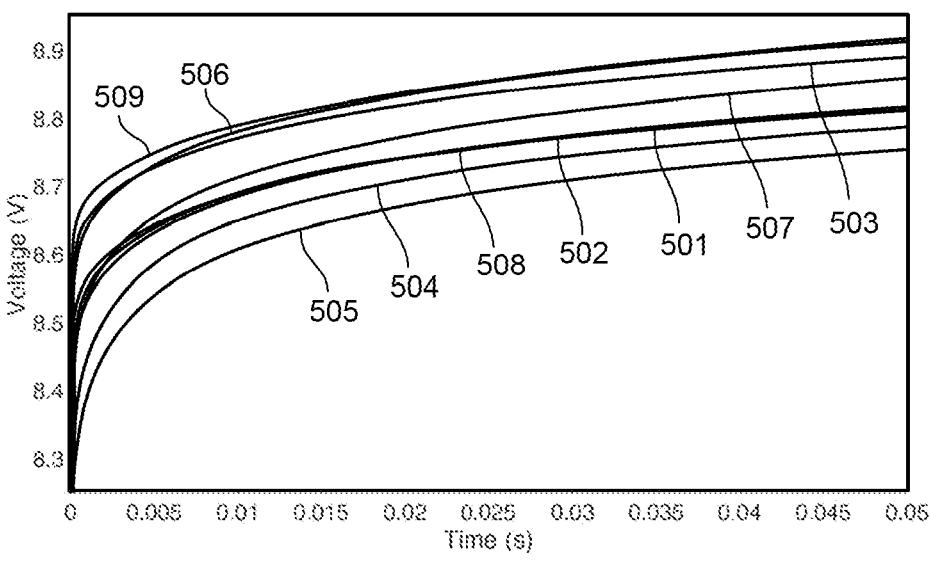
FIG. 16 is a graph showing changes of resistance with time during heating of a resistive element in contact with different porcine organs.

FIG. 16 depicts data obtained from experiments involving inserting the needle probe 30 into different porcine organs. The data demonstrates further that the needle probe 30 is sensitive to different tissue types. The different curves are marked as follows: liver at 11.2 degrees C. (501); heart at 9 degrees C. (502); lungs at 13.5 degrees C. (503); aorta at 11.2 degrees C. (504); oesophagus at 13.5 degrees C. (505); larynx at 11 degrees C. (506); trachea at 11.7 degrees C. (507); thyroid at 13.7 degrees C. (508); and pleura at 11 degrees C. (509).

The experiments providing the data of FIG. 14-16 were all performed on dead tissue. Differences in thermal product between different tissue types are expected to be even larger for living tissue due to the presence of different reaction products/concentrations due to differences in metabolism. Metabolism in cancer cells, for example, is often very different to the metabolism of surrounding cells, leading to markedly different levels of $CO_2$ for example.

We claim:

1. A method of detecting a medically abnormal portion of human or animal skin, comprising:

bringing a resistive element of a probe element into contact with a target portion of the human or animal skin;

driving an electrical current through the resistive element to apply heating to the resistive element while the resistive element is in contact with the target portion;

measuring an electrical response of the resistive element to the heating; and determining, using a processing unit, a heat transfer characteristic of the target portion based on a variation in a temperature of the resistive element against time represented by the electrical response, wherein the heat transfer characteristic represents how efficiently heat is conducted away from the resistive element; and determining, using the processing unit, that the target portion is medically abnormal based on the determined heat transfer characteristic.

2. The method of claim 1, wherein the heat transfer characteristic of the target portion is determined at a plurality of different times and the using the determined heat transfer characteristic to detect whether the target portion is medically abnormal comprises detecting a change in a composition of the target portion over time that is indicative of the target portion being medically abnormal.

3. The method of claim 1, wherein the target portion comprises a mole or other irregularity on the human or animal skin.

4. The method of claim 1, further comprising:

bringing the resistive element into contact with one other portion of the human or animal skin different from the target portion; driving the electrical current through the resistive element to apply heating to the resistive element while the resistive element is in contact with the one other portion of the human or animal skin different from the target portion; measuring an electrical response of the resistive element to the heating; and determining, using the processing unit, the heat transfer characteristic of the one other portion of the human or animal skin different from the target portion based on the variation in the temperature of the resistive element against time represented by the electrical response, wherein determining whether the target portion is medically abnormal comprises detecting a difference in the heat transfer characteristic in the target portion, in comparison to the heat transfer characteristic of the one other portion of the human or animal skin different from the target portion.

5. The method of claim 4, wherein the target portion is a first mole on the human or animal skin and the one other portion of the human or animal skin is a second mole on the human or animal skin, or the target portion is a first irregularity on the human or animal skin and the one other portion of the human or animal skin is a second irregularity on the human or animal skin.

6. The method of claim 1, wherein the heat transfer characteristic comprises the thermal product, $\sqrt{\rho c \kappa}$, where $\rho$ is the density, c is the specific heat capacity, and $\kappa$ is the thermal conductivity.

* * * * *